(12) United States Patent
Reiss

(10) Patent No.: US 7,514,269 B1
(45) Date of Patent: Apr. 7, 2009

(54) PRECISION ADAPTABLE CHEMICAL SPECTROMETER

(75) Inventor: Keith W. Reiss, Fairfax, VA (US)

(73) Assignee: Smart Transitions, LLC, Oakton, VA (US)

(*) Notice: Subject to any disclaimer, the term of this patent is extended or adjusted under 35 U.S.C. 154(b) by 791 days.

(21) Appl. No.: 10/607,532

(22) Filed: Jun. 27, 2003

Related U.S. Application Data

(60) Provisional application No. 60/391,770, filed on Jun. 27, 2002.

(51) Int. Cl.
G01N 33/00 (2006.01)
G01N 27/64 (2006.01)
G01N 1/22 (2006.01)

(52) U.S. Cl. .......... 436/181; 324/633; 324/636; 324/639; 324/640; 324/647; 422/83; 422/88; 422/98; 436/38; 436/173; 436/183

(58) Field of Classification Search .......... 324/633, 324/636, 639–640, 647; 422/83, 88, 98; 436/38, 173, 181, 183
See application file for complete search history.

(56) References Cited

U.S. PATENT DOCUMENTS

| | | | | |
|---|---|---|---|---|
| 2,457,673 A | * | 12/1948 | Hershberger | 324/636 |
| 2,524,290 A | * | 10/1950 | Hershberger | 324/636 |
| 2,792,548 A | * | 5/1957 | Hershberger | 324/636 |
| 3,456,185 A | * | 7/1969 | Akao et al. | 324/636 |
| 3,691,453 A | * | 9/1972 | Rupp et al. | 324/316 |
| 3,691,454 A | * | 9/1972 | Hrubesh et al. | 324/316 |
| 4,181,437 A | * | 1/1980 | Rossiter | 356/246 |
| 4,364,008 A | * | 12/1982 | Jacques | 324/636 |
| 4,482,634 A | * | 11/1984 | Davis et al. | 436/31 |
| 4,703,273 A | * | 10/1987 | Kolbe et al. | 324/314 |
| 4,711,765 A | * | 12/1987 | Cates et al. | 422/89 |
| 4,759,210 A | * | 7/1988 | Wohltjen | 73/31.07 |
| 4,896,097 A | * | 1/1990 | Berger et al. | 324/639 |
| 4,998,433 A | * | 3/1991 | Stumpf et al. | 73/25.01 |

(Continued)

FOREIGN PATENT DOCUMENTS

GB  2271179  * 4/1994

OTHER PUBLICATIONS

Carter, R. L. et al, Physical Review 1947, 72, 1265-1266.*

(Continued)

*Primary Examiner*—Arlen Soderquist
(74) *Attorney, Agent, or Firm*—Novak Druce & Quigg, LLC

(57) ABSTRACT

The invention is directed to a spectrometer for measuring submillimeter absorption. The spectrometer may include a solid state exciter generating a submillimeter wave and sweeping a predetermined frequency band, a frequency marker generating unit electrically generating frequency markers, a sample cell to contain a gas, and a solid-state detector detecting a submillimeter absorption of the gas. A spectrometer energizes a solid-state oscillator to generate a submillimeter wave and to sweep a predetermined band of frequency. The submillimeter wave is introduced into a sample cell containing a gas and frequency markers that are electrically generated during the sweep. Outputs of a solid-state detector disposed in the sample cell are read and recorded as a function of time and with the frequency markers. The recorded outputs of the solid-state detector are converted into a function of frequency using the recorded frequency markers.

29 Claims, 11 Drawing Sheets

U.S. PATENT DOCUMENTS

| | | | | |
|---|---|---|---|---|
| 5,057,782 | A * | 10/1991 | Brown et al. | 324/639 |
| 5,059,927 | A * | 10/1991 | Cohen | 331/77 |
| 5,124,653 | A * | 6/1992 | Andresen et al. | 326/636 |
| 5,198,776 | A * | 3/1993 | Carr | 324/639 |
| 5,548,217 | A * | 8/1996 | Gibson et al. | 324/316 |
| 5,703,365 | A | 12/1997 | Ishihara et al. | |
| 5,748,309 | A * | 5/1998 | van der Weide et al. | 356/326 |
| 5,831,439 | A * | 11/1998 | Suenram et al. | 324/636 |
| 6,012,675 | A * | 1/2000 | Cocatre-Zilgien | 244/16 |
| 6,182,011 | B1 * | 1/2001 | Ward | 701/213 |
| 6,281,801 | B1 * | 8/2001 | Cherry et al. | 340/605 |
| 6,438,499 | B1 | 8/2002 | Hayashi | |
| 6,888,342 | B2 * | 5/2005 | Bradley | 324/76.19 |

OTHER PUBLICATIONS

Costain, C. C., Canadian Journal of Physics 1957, 35, 241-247.*
Radford, H. E., Review of Scientific Instruments 1966, 37, 790-792.*
Britt, C. O., Review of Scientific Instruments 1967, 38, 1496-1501.*
Cuthbert, J. et al, Journal of Physics E: Scientific Instruments 1972, 5, 698-704.*
Schiek, B. et al, Conference Proceedings—European Microwave Conference, 7th 1977, 251-255, Publisher: Microwave Exhibitions Publications Ltd., Sevenoaks, England.*
Schiek, B. et al, Journal of Microwave Power 1977, 12, 347-359.*
Hrubesh, L. W., Applied Spectroscopy 1978, 32, 425-429.*
Gandhi, O. P. et al, Bioelectromagnetics 1980, 1, 285-298.*
Endo, Y. et al, Journal of Chemical Physics 1981, 75, 4379-4384.*
Schafer, E. et al, Berichte der Bunsen-Gesellschaft 1983, 87, 327-334.*
Endo, Y. et al, Canadian Journal of Physics 1984, 62, 1347-1360.*
Taylor, J. A. et al, International Journal of Infrared and Millimeter Waves 1985, 6, 687-695.*
Isaacs, N. A. et al, Review of Scientific Instruments 1986, 57, 414-416.*
Ziurys, L. M. et al, Review of Scientific Instruments 1994, 65, 1517-1522.*
Krupnov, A. F. et al, Journal of Molecular Spectroscopy 1995, 170, 279-284.*
Harmony, M. D. et al, Review of Scientific Instruments 1995, 66, 5196-5202.*
Zhu, Z. et al, Review of Scientific Instruments 1996, 67, 2496-2501.*
Petkie, D. T. et al, Review of Scientific Instruments 1997, 68, 1675-1683.*
Lewen, F. et al, Review of Scientific Instruments 1998, 69, 32-39.*
Suenram, R. D. et al, Review of Scientific Instruments 1999, 70, 2127-2135.*
Van Der Weide, D. W. et al, SPIE 1999, 3828, 276-284.*
Schitov, A. M. et al, International Journal of Infrared and Millimeter Waves 2000, 21, 1479-1488.*
Van Der Weide, D. W., NATO Science Series, II: Mathematics, Physics and Chemistry 2001, 27, 301-314.*
Low, W. et al, Bulletin of the Research Council of Israel 1955, 5A, 40-45.*
Hrubesh, L. et al, Report 1976, UCID-17174, 27 pp. Avail.: NTIS From: ERDA Energy Res. Abstr. 1976, 1(11), Abstr. No. 24377.*
Valkenburg, E.P. et al, Proceedings of the IEEE 1966, 54, 493-498.*
Winnewisser, M., Zeitschrift fuer Angewandte Physik 1971, 30, 359-370.*
Winnewisser, M. et al, Journal of Molecular Spectroscopy 1972, 41 143-176.*
Manning, E. G. et al, Review of Scientific Instruments 1972, 43. 324-326.*
Crosmer, W. E. et al, Review of Scientific Instruments 1973, 44, 837-843.*
Hoefer, W. J. et al, Electronics Letters 1974, 10, 123-124.*
Winnewisser, M. et al, Zeitschrift fuer Naturforschung, Teil A: Astrophysik, Physik und Physikalische Chemie (1974), 29(4), 633-640.*
Des Marais, D. J., Analytical Chemistry 1978, 50, 1405-1406.*
Helms, D. A. et al, Journal of Physical Chemistry 1980, 84, 1758-1765.*
Zhang, G. et al, Chemical Abstracts 1985, 103, abstract 32665a.*
Frankel, D. J. et al, Review of Scientific Instruments 1993, 64, 2368-2370.*
Szpunar-Lobinska, J. et al, Mikrochimica Acta 1994, 113), 287-298.*
Ceulemans, M. et al, Journal of Analytical Atomic Spectrometry 1996, 11, 201-206.*
Burguera, J. L. et al, Talanta 1998, 45, 531-542.*
Pereiro, I. R. et al, Analytical Chemistry 1998, 70, 4063-4069.*
Kminek, G. et al, Planetary and Space Science 2000, 48, 1087-1091.*
Shen, Y.C. et al, IEEE Tenth International Conference on Terahertz Electronics Proceedings 2002, 165-168.*
Albert, S. et al, FASSST: A New Gas-Phase Analytical Tool, Ananytical Chemistry News & Features, Nov. 1, 1998, 719.

* cited by examiner

PRIOR ART

PRECISION ADAPTABLE CHEMICAL SPECTROMETER

REFERENCE TO RELATED APPLICATIONS

This application claims priority to U.S. Provisional Application No. 60/391,770, entitled "Integrated Remote Chemical Spectrometer" filed Jun. 27, 2002, which is hereby entirely and completely incorporated by reference.

BACKGROUND

1. Field of the Invention

This invention is directed to spectrometers that fosters and detects absorptions in submillimeter wave region, and to methods for processing spectroscopic data with unique algorithm.

2. Description of the Background

Spectroscopy using submillimeter wave, or microwave, has the potential to be a potent diagnostic tool. Molecules having a permanent or induced dipole moment have discrete rotational energy levels that can absorb electromagnetic waves in MHz to THz regions. Because of the abundance of rotational energy levels that are unique to the structure of the molecule detected, submillimeter spectroscopy makes it possible to identify chemical species with excellent specificity. One of the earliest studies in this filed was reported almost 50 years ago; "The use of microwave spectroscopy for chemical analysis," C. H. Townes and A. L. Schawlow, chapter 18, "Microwave Spectroscopy," McGraw-Hill, 1995. However, this analytical method did not result in a wide spread use in research communities and industries, partially because the complexity of the instrumentation and associated high cost and maintenance issues.

Recently, with the advancement of THz technologies and computer based system control, submillimeter spectrometers with more practical use have been developed. Such spectrometers are reported, for example, in "A Fast Scan Submillimeter Spectroscopic Technique," D. T. Petkie, T. M. Goyette, R. P. A. Bettens, S. P. Belov, S. Albert, P. Helminger, and F. C. De Lucia, Rev. Scient. Instrum 68, 1675-1683 (1997), and "FASSST: A new Gas-Phase Analytical Tool," S. Albert, D. T. Petkie, R. P. A. Bettens, S. P. Belov, and F. C. De Lucia, Anal. Chem. 70, 719A-727A (1998).

This type of spectroscopic technique was initially made possible by a combination of fast scanning voltage tunable Backward Wave Oscillators (BWOs), optical calibration methods, and modern fast digitization and computation techniques. FIG. 1 shows a diagram of such a spectrometer. Briefly, the BWOs are voltage tunable (~1500-4000 V) tubes covering roughly 0.1-1.0 THz, in bands. A typical tube, an OB-30, covers ~250-350 GHz as the voltage is swept over this range. In this system the output of the BWO is split, with about 10% going to a Fabry-Perot cavity to provide optical calibration, while the rest is used to interrogate the sample. The portion of the power then passes through the sample cell and is detected by an InSb detector. In operation, the tuning voltage is ramped to provide an analog sweep in frequency, and the outputs of the signal detector and FP detector are recorded in parallel.

A typical sweep time is one second and the frequency width 10-100 GHz. This frequency interval contains ~$10^5$ independent resolution elements. With integration times of 1 microsecond, S/N ratios of $10^4$ are obtained.

The system concept is based on the short term spectral purity of the BWO ($Q>10^7$). Because of this spectral purity, the slow and complex phase lock that is ordinarily used to stabilize and control THz spectroscopic systems is not fundamentally necessary. In this spectrometer, the high spectral purity source is swept so rapidly that slow instabilities (associated with thermal drift, etc) are frozen on the time scale of a measurement cycle. Fast digitization records the output of the FP cavity and spectrometer in parallel and makes possible accurate frequency calibration even with thermal drifts, power supply ripple, and nonlinear frequency sweeps. In some sense, the speed of the digitization plays the same role as the bandwidth of a more traditional phase lock loop.

The scanning speed combined with the high spectral brightness (W/Hz) of electronic sources and the very strong molecular interactions in the THz range, rapidly produces analytical fingerprints with remarkable information content. This is illustrated in FIG. 2, which is presented as a series of blow-ups in both frequency and amplitude.

FIG. 2 shows about a 25 GHz region of the spectrum of $HNO_3$, which was recorded in 1 second. The middle and lower figures show expansions of this spectrum.

Stated another way, if the upper figure were plotted with 1 mm of noise in the vertical and 1 cm of width per resolution element in the horizontal, it would require a piece of paper 10 m high and 1 km long for each second of data acquisition.

The high resolution of the millimeter spectroscopy comes about because the Doppler broadening (which is the fundamental limit in most systems) is proportional to frequency. Thus, lines in THz spectra are about 100 times narrower than those in infrared spectra. For example, for molecules of about the size of $ClONO_2$, their spectra are unresolvable in the infrared. Rather than the detailed rotational spectra shown in FIG. 3, only a broad band is observable in a infrared spectrum. Because of the high resolution in the THz, the optimum pressure (set by the condition that the Doppler and pressure broadening be approximately equal) is much lower, typically 10-50 mTorr.

One of the disadvantages of this spectrometer is, however, its size. The Fabry-Perot cavity alone occupies a space as large as a small room. In addition, BWO and associated magnets for guiding electrons as well as the InSb electron bolometer that needs to operate at 1.5 K require plenty of space for its instrumentation. Because of its excellent specificity and speed, the submillimeter spectrometer is theoretically suited for applications outside laboratories such as remote chemical analysis. However, at least the large size has prevented the submillimeter spectrometer from being seriously considered for such applications.

SUMMARY OF THE INVENTION

The invention overcomes the problems and disadvantages associated with current designs of the submillimeter spectrometers and provides a new compact submillimeter spectrometers and methods for identifying chemical species using the spectrometer.

One embodiment of the invention is directed to a spectrometer for measuring submillimeter absorption. The spectrometer includes a solid state exciter generating a submillimeter wave and sweeping a predetermined frequency band, a frequency marker generating unit electrically generating frequency markers, a sample cell to contain a gas, and a solid state detector detecting a submillimeter absorption of the gas.

Another embodiment of the invention is directed to a spectroscopic method that includes energizing a solid sate oscillator to generate a submillimeter wave and to sweep a predetermined frequency band, introducing the submillimeter wave during the sweep into a sample cell that contains a gas, electrically generating frequency markers sequentially during the sweep, reading during the sweep outputs of a solid state detector disposed in the sample cell and detecting an absorption of the gas, recording the read outputs of the solid state detector as a function of time and recording the frequency markers as a function of time, and converting the recorded outputs of the solid state detector into a function of frequency using the recorded frequency markers.

Another embodiment of the invention is directed to a method of measuring submillimeter absorption. The method includes introducing a gas containing a chemical species of interest into a trap, cooling the trap so that the chemical species is in a condensed state, reduce the pressure of the trap to evacuate the remainder of the gas that is not condensed, heating the trap to a first temperature so that the chemical species evaporates, leading the evaporated chemical species into a sample cell, and measuring absorption of the chemical species.

Another embodiment of the invention is directed to a method of surveying an area for a chemical species. The method includes taking air into a spectrometer at a first location, receiving global positioning system (GPS) coordinates at the first location, measuring a submillimeter absorption spectrum of the air taken in at the first location, recording the absorption spectrum of the first location with the GPS coordinates of the first location, taking air into a spectrometer at a second location, receiving GPS coordinates at the second location, measuring a submillimeter absorption spectrum of the air taken in at the second location, and recording the absorption spectrum of the second location with the GPS coordinates of the second location.

Yet, another embodiment of the invention is directed to a method of determining a presence of a chemical species in a mixture of gasses. The method includes introducing the mixture of gasses into a sample cell, irradiating the mixture of gasses in the sample cell with a submillimeter wave that sweeps a predetermined frequency band, generating a submillimeter spectrum of the mixture of gasses, providing a standard submillimeter spectrum of the chemical species that is obtained from the chemical species of a pure form, selecting a first peak of the standard submillimeter spectrum of the chemical species, and determining whether the selected first peak is present in the generated submillimeter spectrum of the mixture of gasses.

Other embodiments and advantages of the invention are set forth in the description, which follows, and in part, may be obvious from this description, or may be learned from the practice of the invention.

DESCRIPTION OF THE INVENTION

As embodied and broadly described herein, the invention is directed to a method for processing spectroscopic data with unique algorithms and a compact submillimeter spectrometer based on these algorithms.

Figure 1:
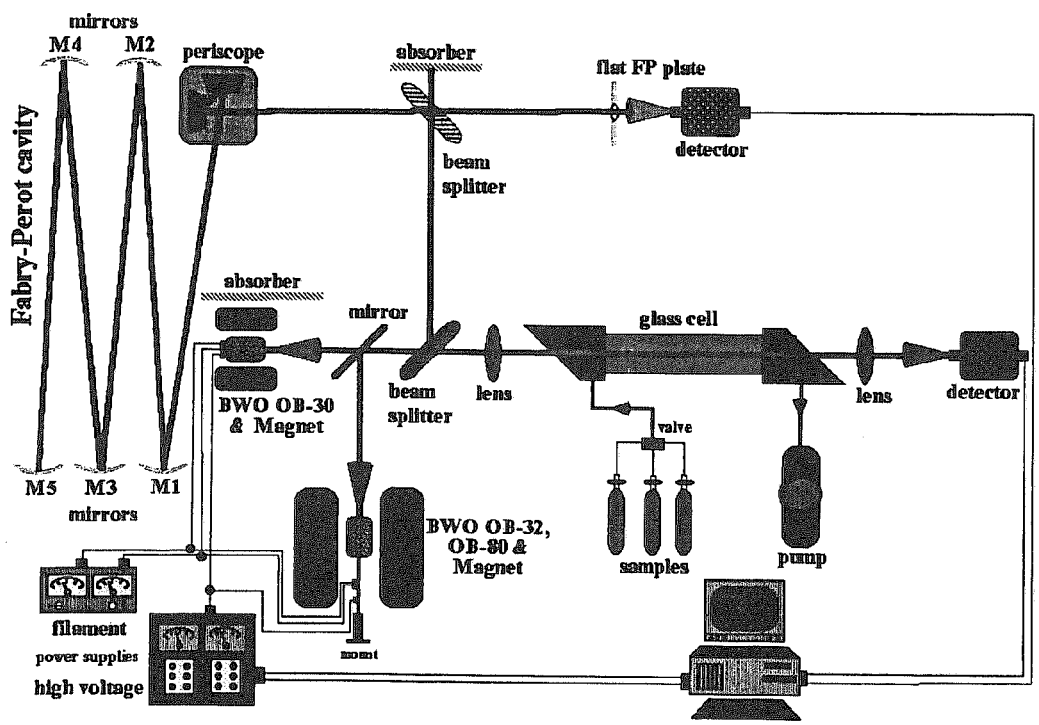
FIG. 1 is a system diagram of a conventional submillimeter spectrometer.

A submillimeter spectrometer, such as shown in FIG. 1, has been used in laboratory settings to investigate absorptions in submillimeter wave region. That is, a fluid sample, which may be a gas, a liquid, or an aerosol, is prepared prior to the spectroscopic measurement so that the fluid contains only a single chemical species or majority of the fluid is the single chemical species. However, the submillimeter spectrometer has not previously been utilized to identify a single chemical spices in a fluid mixture that contains the chemical species as well as other major and minor ingredients.

Figure 4:
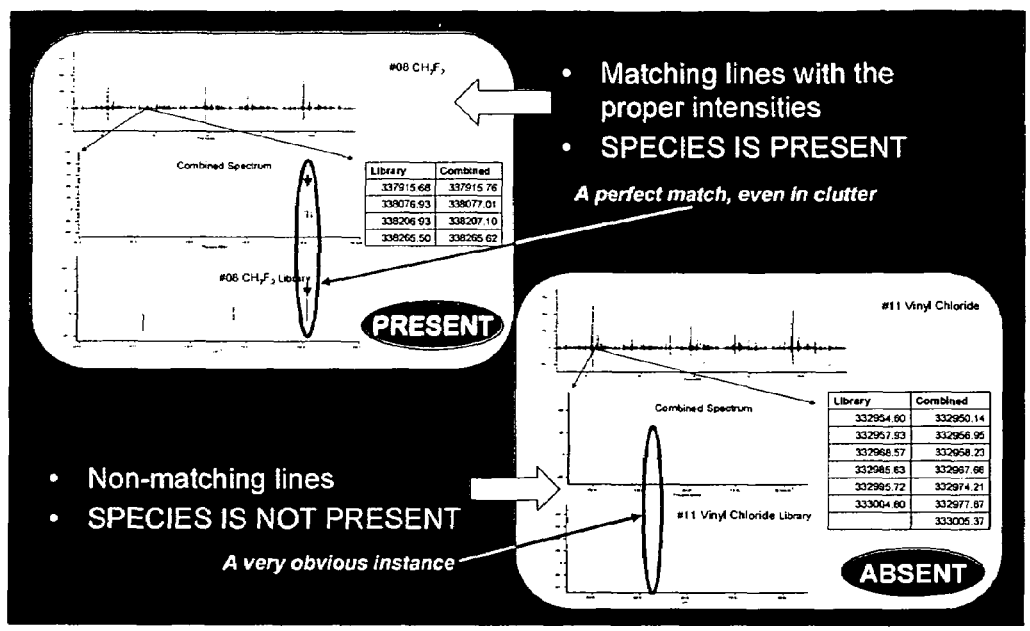
FIG. 4 compares spectra of a gas mixture taken with and without a specific chemical species.

FIG. 4 is a result of spectroscopic measurements directed to identifying a single chemical species in a gas mixture. A segmented sample cell with twenty-one (21) separate vacuum segments along the optical path, was constructed to keep separate the various possibly reactive chemical species within a sample. This sample cell was incorporated into the submillimeter spectrometer shown in FIG. 1. Cells may further contain one or more agents to inhibit interaction between chemical species with a sample. Agents may be incorporated into the cell structure, layered onto the inner surface of the cell, or added to the sample at any stage. Agents may be general inhibitors of all chemical interaction, or specifically targeted to inhibit only specific chemical reactions. Alternatively, the sample within the cell may be exposed to conditions to minimize or substantially inhibit general or specific interaction between chemical species of interest. Such conditions include, but are not limited to, extremes in temperature, pressure or exposure to radiation of defined wavelengths.

In this experiment, 30 chemically library spectra were provided and compared to composite spectra of 19 chemical spices. In addition, the first segment was used to contain $SO_2$ for registering the Fabry-Perot fringes, and the last segment contained the atmospheric "soup" for the clutter aspect of the experiment. The target chemical spices of the experiments shown in FIG. 4 were $CH_2F_2$ and vinyl chloride. Despite the presence of other 18 chemical spices in the gas, the presence or absence of the species of interest from the overall mixture was confirmed. There was an immense degree of spectral information content in the top overall spectrum for each gas. The lower zoomed views, which show only about one percent (1%) of the data on a still compressed scale, provided easy spectral identification substantially without influence of other species present. Many such intervals can be examined with similar conclusions. The information is very abundant so that it is essentially multiply redundant. The abundance of usable spectral information provides redundancy in detection/identification opportunities, thus providing high sensor performance in false alarms (i.e., misidentifications) and detection probability (i.e., given the true presence of a candidate species). This spectrometer system may be used to create a spectrum library that is used with a compact spectrometer, such as described herein.

Figure 5:
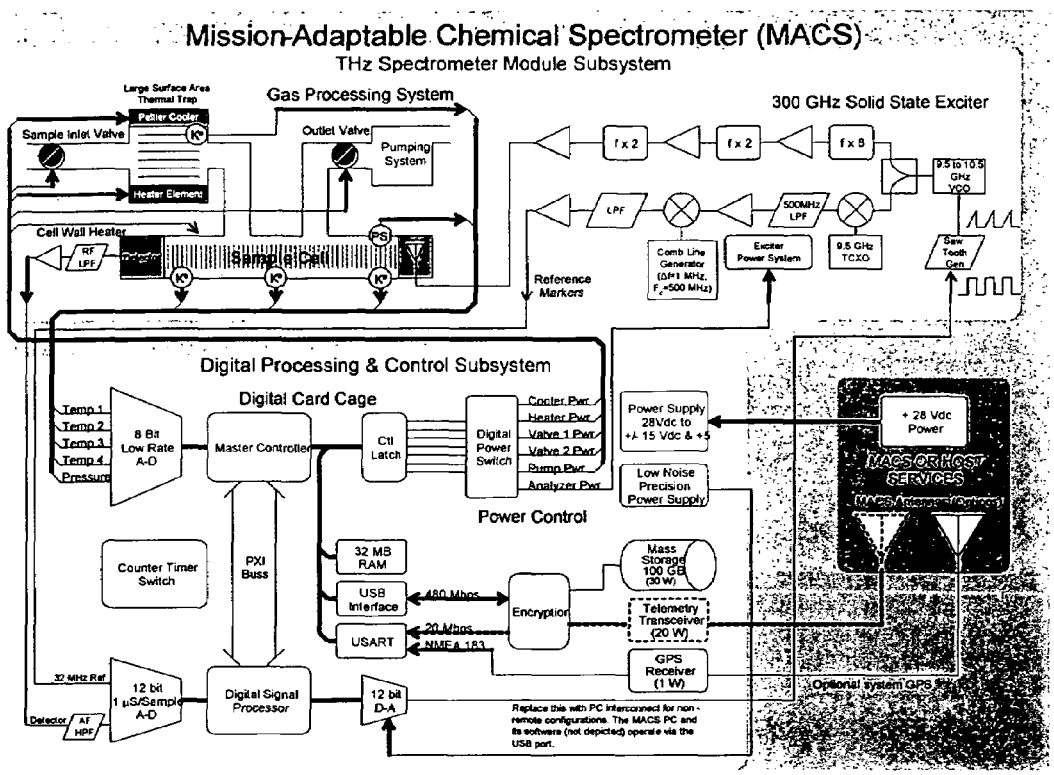
FIG. 5 is a system diagram of a submillimeter spectrometer of an embodiment of this invention.

FIG. 5 shows the overall system design of a submillimeter spectrometer of an embodiment of the invention. The system is divided into two subsystems, i.e., THz module subsystem and digital processing and control subsystem. The THz subsystem includes a gas process unit having a gas trap, a sample cell for spectroscopic measurement and gas outlet unit as well as a solid state exciter coupled with an electronic reference system. A gas to be examined, or most likely a mixture of gasses that may include a gas of interest, is led into the gas trap. The gas is trapped in the gas trap under cooling to separate it from other chemical elements of the mixture, and then heated to evaporate into the sample cell. The all solid-state exciter generates a submillimeter incident wave of 300 GHz, and, at the same time, reference markers for calibration are generated by the associated electronic reference system. The frequency markers are generally of the same frequency throughout a measurement. Exact value of the frequency marker may depend on the overall system design. For example, it may be 100 KHz, 1 MHz, 10 MHz, 25 MHz, 35 MHz or the like. The signals from a diode detector located in the sample cell and the corresponding reference markers are stored in the digital processing and control subsystem. This subsystem also controls the exciter, the electronic reference system and the gas process unit.

The principle of detecting absorption peaks corresponding to the rotational energy level(s) is the same as that of the spectrometer with the BWO and Fabry-Perot cavity shown in FIG. 1. However, in this embodiment, the radiation source, BWO, is replaced by the compact solid state exciter, and the optical reference system, Fabry-Perot cavity, is replaced by the electronic reference system. In addition, the InSb electron bolometer is also replaced by the Schottky diode. Accordingly, the overall size of the spectrometer is significantly reduced. Preferably, the spectrometer of this invention has a size small enough to be deployed in a wide variety of field applications and may be portable such that it can be carried by a single individual, and easily packaged. Suitable sizes are about five (5) square meters, about two (2) square meters, about one (1) square meter, about one half (½) a square meter, about one hundred (100) square centimeters, or even less. Suitable weights are less than two hundred (200) kilograms, less than one hundred (100) kilograms, less than fifty (50) kilograms, less than twenty five (25) kilograms, less than ten (10) kilograms, and less than five (5) kilograms.

Components of the solid-state exciter may be chosen from those currently available commercially. The generation of the radiation wave starts with a 10-20 GHz VCO or a 5-10 GHz VCO. In addition VCXOs may be used. Several VCOs were tested and found to have the required spectral purity ($<10^{-6}$) and tuning range. These VCOs have considerably more linear tuning than the BWOs, which simplifies the frequency calibration. The VCO of 1 mW drives an active multiplier chain to produce 40 mW near 100 GHz, followed either by one stage of a passive diode frequency doubler or tripler, or two frequency doublers in tandem. This system will occupy a few 10s of cm$^3$ and require ~10V.

With 1 mW of available source power, the InSb bolometer detectors are driven far into saturation. Schottky diode detectors are available with responsivities of >1000 V/W. With the drive power available, performances are similar to those of helium detectors. A less sophisticated diode detector at 150 GHz was tested and still found to be superior to the cooled bolometer detectors because it saturates at a higher power level. The Schottky diode shown in FIG. 5 has 1000 mV/mW. Because of the use of solid-state devices in place of Fabry-Perot cavity, BWO and the bolometer, the whole spectrometer system occupies a volume on the order of <1 ft$^3$ with power consumption of <100 W for the entire system. However, a spectrometer with a volume less than 5 ft$^3$ or 10 ft$^3$ would also be useful.

Figure 2:
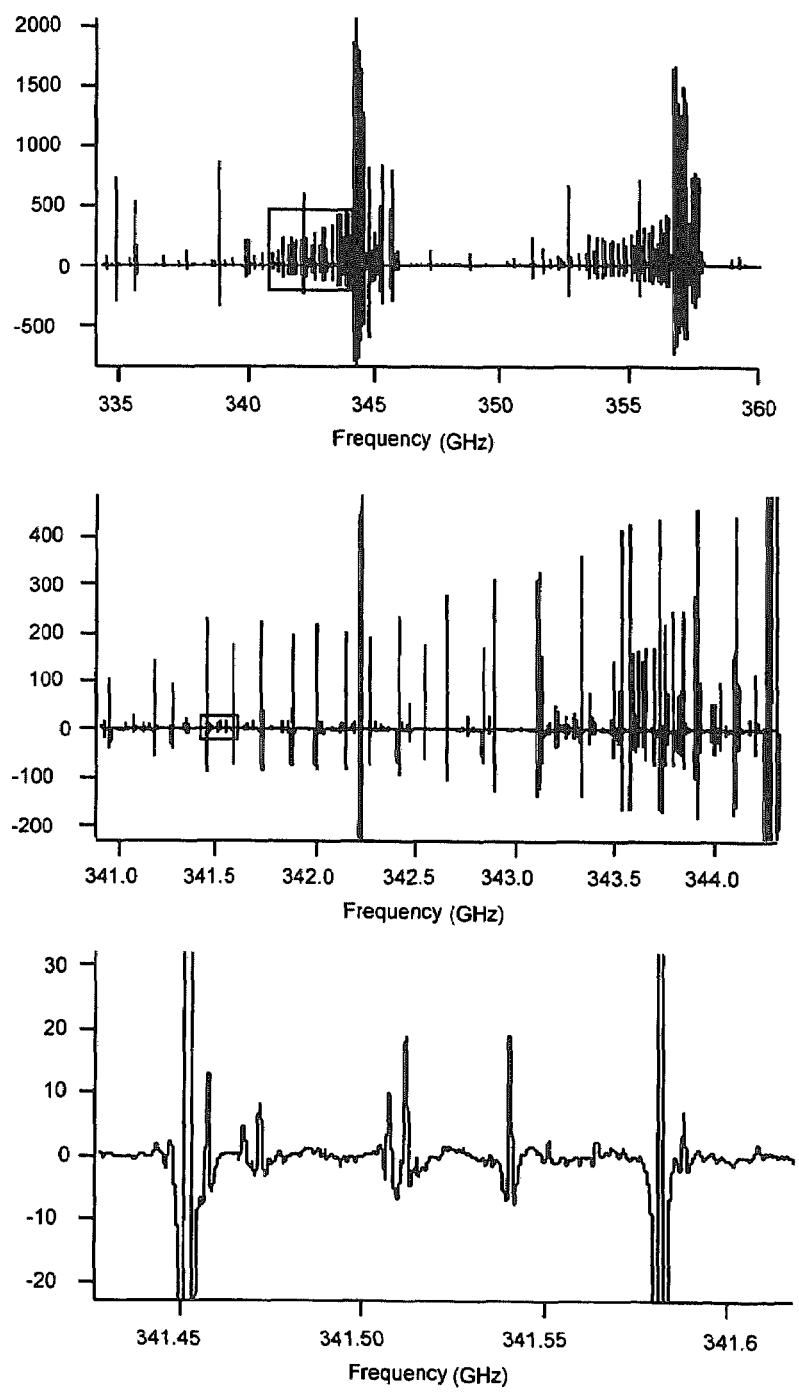
FIG. 2 is an example of spectra taken with the spectrometer of FIG. 1.
Figure 3:
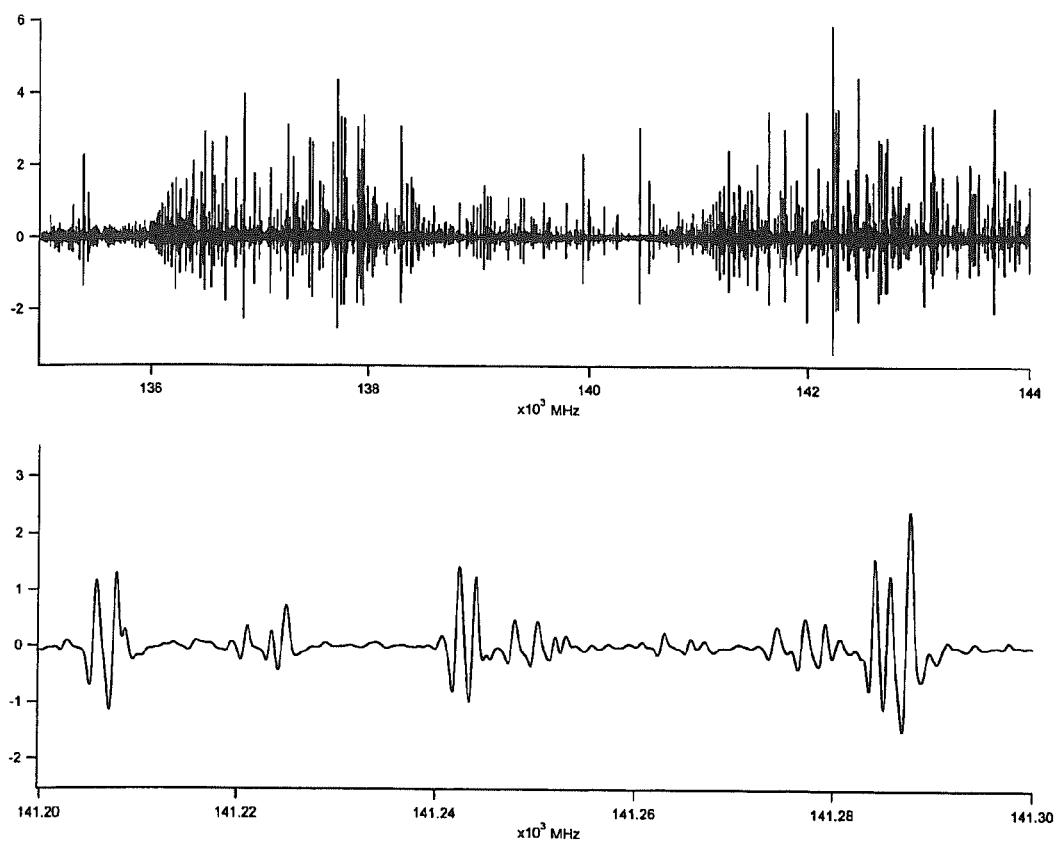
FIG. 3 is another example of the spectra taken with the spectrometer of FIG. 1.

The operation of the THz module is further described herein. The controller of the digital processing and control subsystem sends an approximately linear ramp to the GHz VCO of the THz module, which responds with an approximately linear analog sweep of frequency as a function of time, typically taking ~1 second to produce spectra similar to that shown in top of FIG. 2 or ~0.1 and 0.01 seconds for the smaller subscans shown in FIG. 2. In the example shown in FIG. 5, three multipliers work together to raise the frequency of the incident wave to about 300 GHz for a sweep of a 30 GHz band. The generated submillimeter wave is guided to one end of the sample cell, partially absorbed by the gas species while traveling through the cell that has an absorption effective path length of about one (1) m, and detected by the Schottky diode at the other end of the cell. The frequency markers are generated based on the output of the same 10 GHz oscillator. The integration time for the signal acquisition is about 1 microsecond in this example. In this example, references markers are sequentially generated during the sweep of the 30 GHz band. This corresponds to about 30,000 resolution elements at 300 GHz. The controller digitizes both the output of the spectral channel and frequency marker channel in parallel, and software uses the information in the marker channel to assign a frequency to each time/frequency bin in the spectrum. Thus, simultaneous collection of reference markers within the 30 GHz band pass of the spectrometer allows the time scale to be related back to frequency. This spectrum, calibrated in both frequency and intensity, can then be compared manually with a library, or be used in conjunction with sophisticated algorithms for probability of detection determinations.

Alternatively, there may be a particular gas or gasses of interest and it may be advantageous for the system to spend observation time focused on that gas. In this case, the system can focus its frequency sweep on a subscan or subscans of the entire spectral interval to either achieve greater speed or sensitivity. Because even these subscans contain many resolution elements, in most cases false alarm rates of near zero are still obtained. This is useful especially when the spectrometer system is not able to isolate a chemical species from the mixture taken into the spectrometer. In such an application, a frequency subband is positioned to avoid absorption peaks due to other ingredients of the gas mixture. The width of the subband is, for example, 10 GHz, 5 GHz, 1 GHz, 100 KHz or the like.

The acquired data produces lines at essentially their Doppler line widths (about 1 MHz). This spectrum is digitized and stored in memory at a rate of ~106 data points/sec. Because the optimum pressure for spectroscopy in the THz is low (~10 mTorr or about $10^{-5}$ atmospheres) and because the eventual sample cell volume can be made as small as ~1 cm$^3$, the total sample required is very small. If this small sample is not diluted in a background atmosphere, the signals are very strong, even with the $10^{-6}$ second integrating time.

Figure 6:
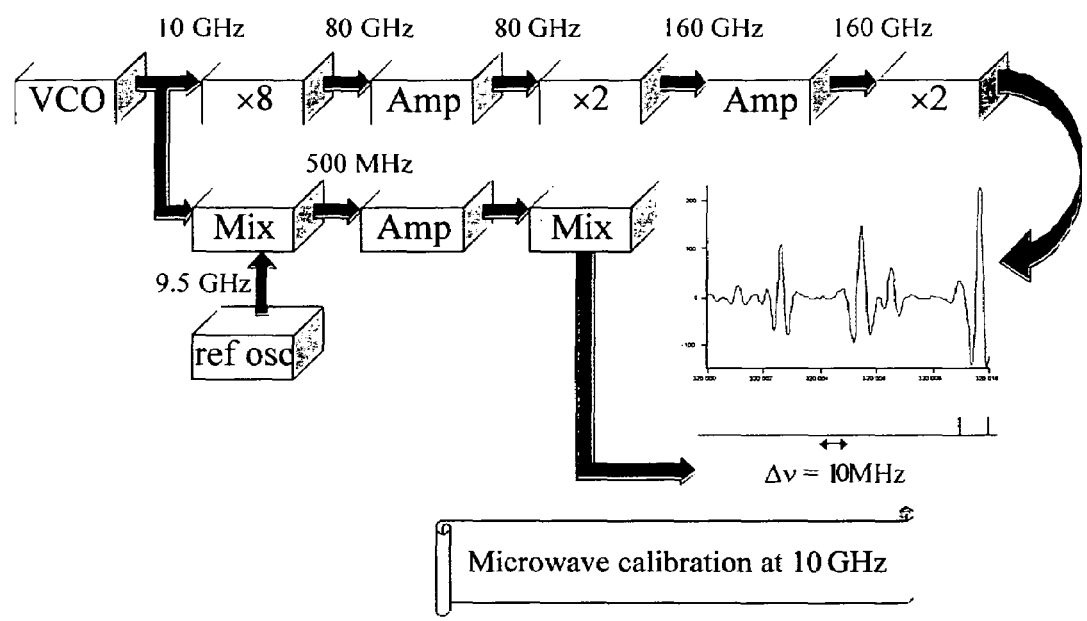
FIG. 6 shows the frequency marker generation unit of the system shown in FIG. 5.

FIG. 6 shows further details of the frequency marker generation scheme shown in FIG. 5. In this example, the scanning VCO is mixed with a crystal based reference at ~10 GHz. The mixing products (±~1 GHz) is amplified and mixed with a 10 MHz comb. The mixing product (±100 kHz) is then amplified and digitized to produce absolute frequency reference points, by interpolation, for the entire spectrum. In addition to the very large size reduction, this is attractive because the solid state system starts with a VCO at a relatively low frequency (~10 GHz). This allows the use of standard microwave components to obtain a frequency reference. However, because of the fast sweep rate, phase information will need to be recovered and processed to provide accurate frequency reference.

Operation of the spectrometer is described with respect to the digital processing and control subsystem. Running a scheduler, the master controller (MC) autonomously regulates the gas processing system to collect a sample starting at a scheduled time or GPS location. The MC opens the collection and outlet valves and enables the cooler within the thermal trap while storing the GPS coordinates. Low vapor pressure samples condense in the thermal trap while the volatiles such as oxygen and nitrogen are pumped through and out of the system. The MC then closes the sample inlet and proceeds to pump down the remaining gas in the sample cell. Upon closing the outlet valve the thermal trap can be heated to boil off all or some of the sample material. Through closed loop monitoring of temperature and pressure data, heat can be applied to maintain a constant vapor pressure of the sample being measured. In this way the MC controls data collection through precision distillation of the collected sample. This allows the collection of several data sets from the same sample at varying vapor pressures.

Once the MC has prepared the sample cell, the MC issues a command to the digital signal processor (DSP) to start data collection. Data collection is initiated when the DSP writes a new output level to the DA converter. This output level parameter is passed to the DSP from the MC in the "start collection" command along with the pulse duration. The change in voltage at the output of the AD causes an integrator in the solid-state exciter to start ramping the VCO, which generates the instrument frequency sweep. At the same time the frequency sweep is induced, the DSP starts simultaneous data collection of the detector voltage and the reference markers. Both channels can be read one million times over the duration of the sweep as defined in the "start collection" command. At the end of the frequency sweep, data collection stops and the output of the DA can be set low. The DSP now processes the data with several options possible.

First, the DSP processes the reference data to locate the reference marker peaks and tags the corresponding detector output. This reduces the data set by fifty percent (50%) while maintaining frequency information. Since the 12 bit data sample takes up a byte and a nibble, the remaining nibble can be used to encode the frequency information directly into the detector sample. The data is then transferred to the MC where it is wrapped with header information containing GPS location and time.

Second, the DSP processes the reference markers as described in first scenario and tags the corresponding detector output. Additionally, the DSP finds the top 30,000 peaks (or fewer if user defined and there are likely to be only a few thousand peaks in the GHz sample) and reports back offset and amplitude sets for each value. The offset is the number of whole marker ticks from the start of the sample along with the fractional tick information in the way of the number of samples past the tick. This reduces the data set to less than five percent (5%) of the first scenario. Note that the maximum number of resolution elements in a 30 GHz region around 300 GHz is about 30,000. This is a completely filled spectrum. The data rate is higher because it takes about ten (10) samples/line width to get some idea of line shape and to help separating signal from noise. Thus, the approach reduces the amount of data by at least a factor of ten (10) or more.

Third, the DSP processes the samples and corrects for frequency sweep non-linearity as described. The processed sample is then compared to a reference library of compounds. Correlation of the current sample to a stored reference defines an alarm condition and the compound information is transmitted to an examination station.

The digital processing and control subsystem is designed to accommodate operation in any one of the above scenarios, providing design flexibility.

Figure 7:
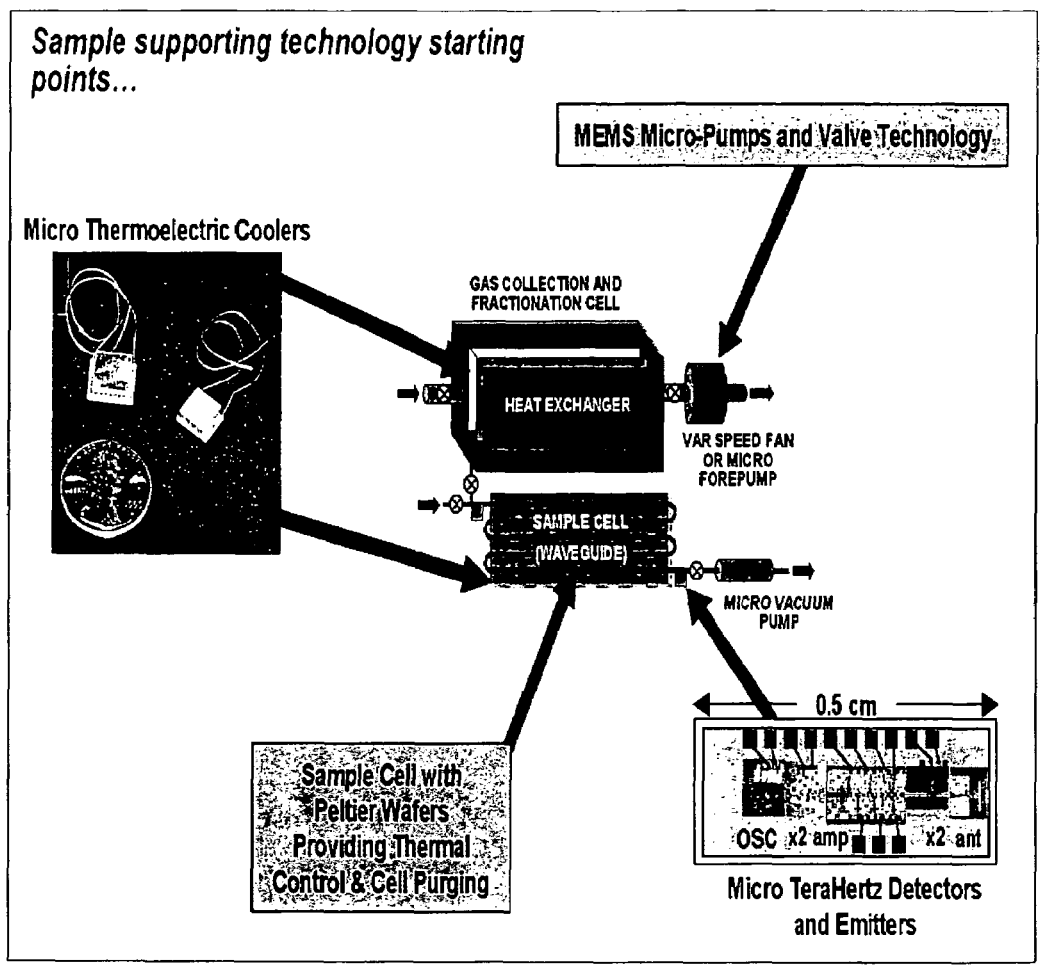
FIG. 7 is a schematic diagram of a gas processing system of the spectrometer of FIG. 5.

FIG. 7 shows an example of the gas processing unit shown in FIG. 5. VAR speed fan or a forepump is used to take the gas samples into the thermal trap, and micro thermoelectric coolers are used to freeze the gas samples in the trap. The optical path for the spectroscopy is formed as a waveguide and has an effective optical path of about 1 m and 1 $cm^2$ cross section in the sample cell. After the measurement, the gas is evacuated to the outside by a micro vacuum pump. In addition, the detectors and the exciters may be as small as 0.5 cm in length.

Figure 8:
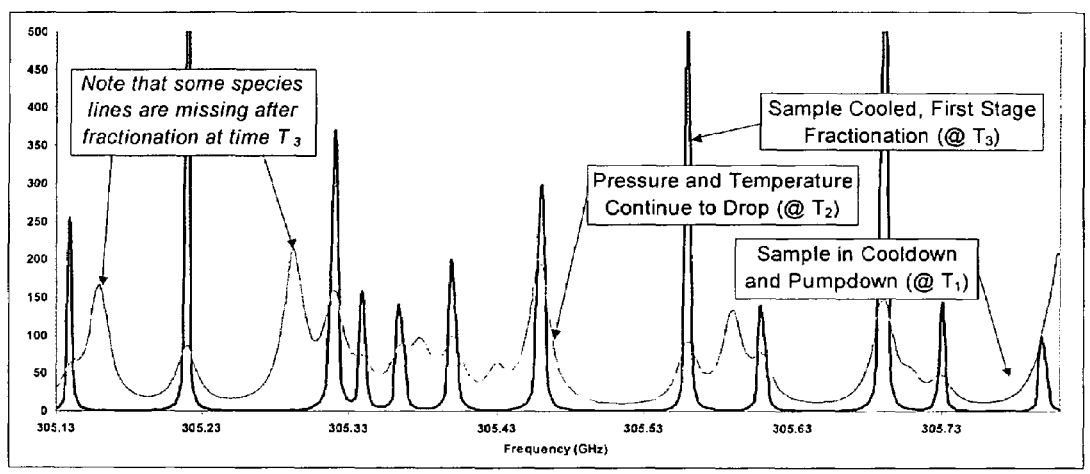
FIG. 8 is a schematic drawing to show the effect of the removal of ambient gas components on the spectrum sensitivity.

In most applications, the gases of interest are diluted in air and are initially ingested. While it is still possible to detect the diluted sample by simply reducing the total pressure to ~10 mTorr (a pressure that is obtainable with simple pumping systems because of the small cell volumes), it is advantageous to selectively remove the components of the ambient air which are not of interest. While a number of collection and concentration approaches have been developed, thermal fractionation used in the gas processing unit shown in FIG. 7 is both a practical and conceptually straightforward approach. Air is ~99% $N_2$ and $O_2$, and since these gases are both much more volatile than virtually all of the gases of interest, a simple trapping and distilling cycle can eliminate the air. FIG. 8 schematically shows the effect of the removal of the ambient gasses on the submillimeter spectrum. During the cool down and the associated pressure reduction, baseline noise level was clearly reduced. In addition, some of the peaks present at the beginning of the cool down disappeared at the end of the process.

While this is a routine operation in the laboratory and even in some field instruments, the spectrometer of this embodiment uses more progressive fractionation to obtain a fast cycle time so as to produce as small a sampling cycle time as possible so that many samples can be taken quickly. This approach is especially attractive when only small samples are requited.

Figure 9:
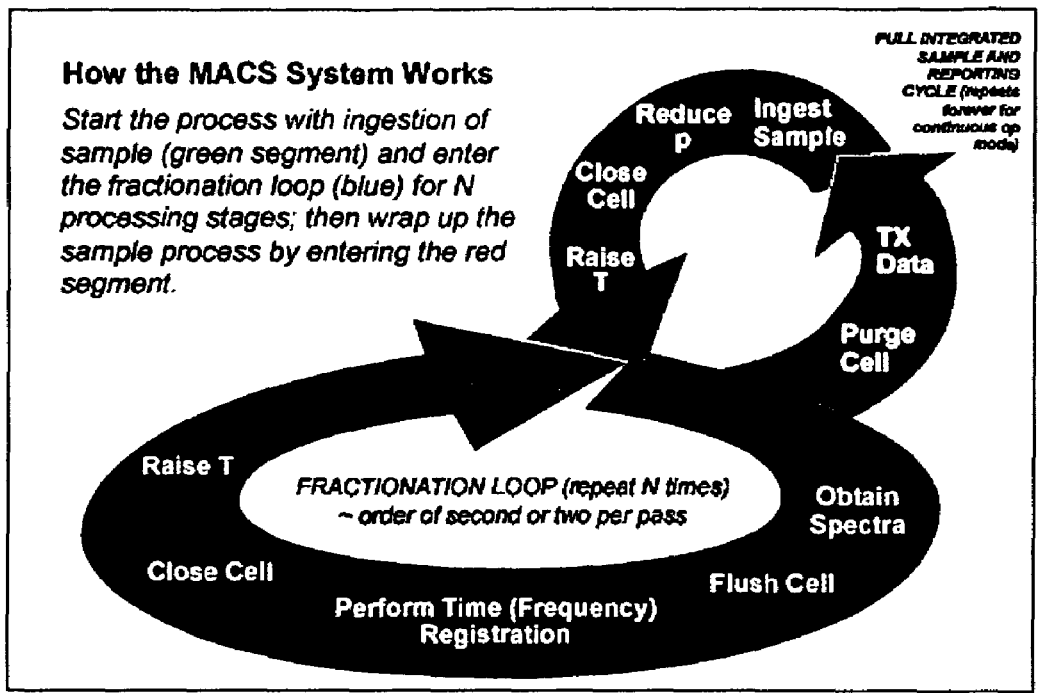
FIG. 9 schematically show a fractionation loop.

This sampling cycle is shown in FIG. 9. The processing may best be considered as a series of "fraction" cycles (the lower loop shown in FIG. 9) operating within a larger loop denoted as the integration and reporting cycle in the same illustration. The gas intake system opens up and pumping begins as the thermal trap is cooled down. When an adequate sample is ingested and the gases of interest are frozen out, the gas inlet valve is closed and pumping removes the nitrogen and oxygen, which if present, induces undesirable pressure broadening (or alternatively, dilution if the total pressure is simply reduced by pumping) of the spectral lines as shown in FIG. 8. Next, the gas exit valve is closed and the frozen sample is warmed slightly (first stage "fraction") and some gas is created that is then probed with radiation from the solid state emitter, thus forming a spectral data set. With the formation of each spectrum, the markers are utilized to interpolatively form a uniform time/frequency baseline. This also facilitates multi scan integration. The cell is flushed and closed and the steps repeated, incrementally increasing the temperature and producing separate spectra for each set of molecular species contained in the respective "fraction." When these cycles are completed, the cell is purged, the data is transmitted to the analyzer and the system prepares to ingest another atmospheric sample. Depending upon the volatility of the gases of interest, the range of temperatures in this cycle can be adjusted in software. In addition, the "fractions" are selected in terms of freezing points (boiling points) of each species in the chemical library associated with the spectrometer, or other criteria based on specific requirements of the application. For most applications, the temperatures can be obtained with small thermoelectric coolers. While this is conceptually the simplest gas capture front end for the spectrometer, its modular design makes the integration of other approaches (including those supplied by end users) straightforward. In remote mobile applications, the resulting composite sample can be tagged with GPS position and time based on platform navigation input or even an internal GPS receiver. The simplified loops in FIG. 9 do not show the integration of multiple scans within a particular fraction, however, this is a sensitivity enhancing option. Sensitivity of the submillimeter spectrometer may be further enhanced by conventional approaches as well as approaches described herein.

First, while there are applications (e.g., the analysis of chemicals from a vessel, munitions, etc.) that produce a concentrated sample of the analyte, there are many important applications in which the chemicals are dispersed in air. In these cases the ultimate sensitivity of any gas analysis device can be increased if the major constituents of air are first removed as described herein. This approach is especially attractive in the THz, because the optimum sample pressure is $\sim 10^{-5}$ atmospheres, thus leading to proportionally small sample requirements.

The major constituents of air, nitrogen and oxygen, are relatively easy to remove because their high volatility and small physical size are rather different from gas samples of interest. If the air in the sample cell is drawn through the trap whose temperature is >77K, the oxygen and nitrogen will pass and the remaining fraction will be trapped. The pumping valve can then be closed and the trapping surface warmed. In the simplest scheme the trap is warmed to 300 K and all of the trapped sample released into the cell. Depending upon cell volumes, pumping speeds, etc. this cycle can be done on a one (1) second to one (1) minute time scale. There are reports in the literature of this thermal cycling being done on time scales of a few milliseconds.

Even in this simple example, the sensitivity is increased by a factor of 100. Only a modestly more complex algorithm makes it possible to look at the fractions that come out of the trap as a function of its temperature as described. While there are limitations on the separation of gases with similar vapor pressures, there are very large, but scenario dependent, gains in detection that can be achieved.

Second, the most straightforward enhancement of the sensitivity is to increase the integration time from one (1) microsecond to a longer period. There are many applications for which it will be unnecessary to look at all 30,000 channels to get absolute specificity and generality. In these, it would be advantageous to look at only a few channels, but with longer integration times. This gain may ultimately be limited by systematic effects that can not be reduced by averaging the spectra. Experience with similar systems has shown that the principle systematic effect comes from baseline variations. These can be traced to multipath interference between different modes as power is transmitted from the THz source to the detector. At least one (1) second integration times is expected to be useful.

There is an even more important issue, optimizing at one (1) sec/resolution element, the trade-offs between speed, sensitivity, and specificity. If one were to integrate the entire spectrum, it would require 106 seconds. However, this is not really necessary and much more optimum approaches exist. For example, most of the weaker species are weak because their spectral intensity is divided among many lines. The automatic recognition software may, in effect, "integrate" these lines together. Accordingly, the long signal integration time for enhancing the sensitivity may not be necessary.

Third, while the one (1) meter effective path length (EPL) of the sample cell is similar to those which have been used for many years, there are enhancements possible to overall system performance that utilize in one of several fashions multipass cells to lengthen the EPL for the absorption. The sensitivity of the system is proportional to the path length of the absorption cell. While this cell can be very simple (e.g., a hollow metal pipe 5 mm in diameter), it would be advantageous to have the absorption length to be as long as possible. This approach may result in an enhancement by a factor of ten (10), one hundred (100) or more.

Fourth, it is useful to optimize the noise spectrum of the room temperature diode detectors and the preamplifier frequency response relative to the system sweep speed (and thus its central data recovery frequency). At a fundamental level a gain here is possible, but unpredictable system noise is an issue and accordingly the potential enhancement for this is estimated as ten (10). Additionally, with the availability of more power in solid state THz exciters, 'autodyne' detection techniques may be used to increase detection sensitivity. Briefly put, power that is greater than that required for molecular saturation can be separately transmitted to the detector, which then plays the role of a mixer (with zero-frequency IF) in a heterodyne system. A similar scheme has been used for many years at lower microwave frequencies in radar speed detection devices.

The signal processing of the spectrometer is further described with reference to FIG. 10. The absorption spectrum is formed through the square law response of the diode detector. The fluctuations in voltage from this device are very rapid by virtue of the sweep rate (e.g., 30 GHz/second). The system instabilities are lessened and additionally a high pass (mid frequency range) filter may be used with cut-off above the practical tuning margin. This yields wobbling baseline reduction and forms first derivative response, which is desirous. Within the detection block, residual RF is cleared prior to application of an LNA. The signal is then digitized through an AD converter. In parallel, the harmonic frequency marker generation circuit produces bit markers in the output that tag the exact positions of a comb line of 10 MHz separations. To complete this stage (segment A of FIG. 10) the software resolves non-linearities in the sweep, interpolating the equi-frequency markers to smooth the now digitized envelope. Implicitly, in this section of the process, built-in spectrometer calibration curves are used to adjust the signal amplitude in order to facilitate eventual concentration measurements, and an absolute frequency anchor is assigned to the comb of marker frequencies. This compensates for non-uniform amplitudes presumed here to be a function only of frequency. These activities are also needed at this processing level to facilitate integration, shown in the figure.

Figure 10:
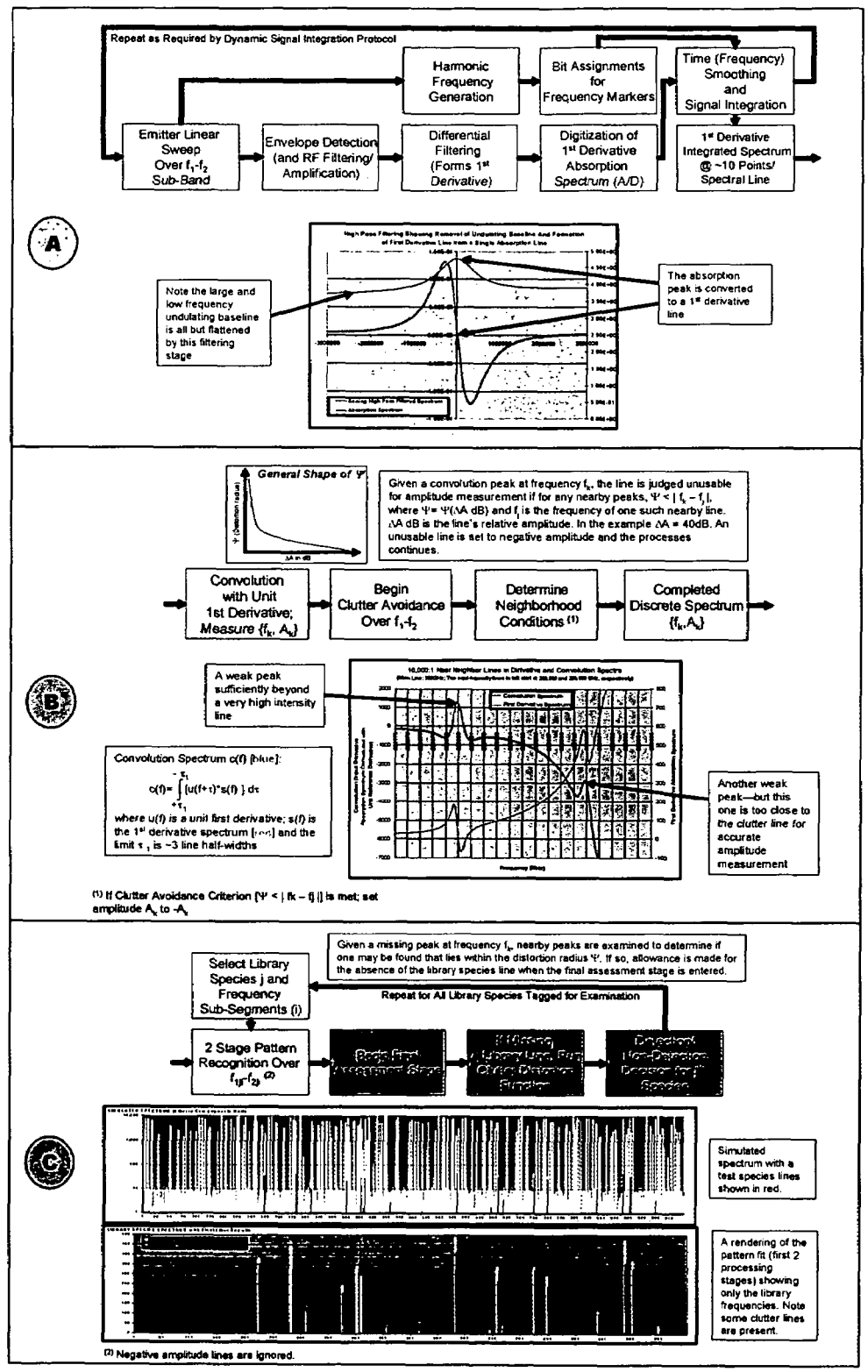
FIG. 10 is a diagram of the signal processing scheme.

As shown in segment B of FIG. 10, the system then operates upon the waveform of first derivative spectral lines by convoluting a unit Lorentzian first derivative with the spectrum using a limited extent of the integral with the extent determined by the level of smoothing desired and the processing time consumed. The resulting lines are essentially second derivatives, the smooth peaks of which are recorded (f,A). A clutter avoidance routine executes next that considers the local distortion of the spectrum at a particular line position by the presence of other spectral lines. The level of disturbance (and thus diminished reliability in amplitude measurements and to an extent also frequency) can be determined and used to define the clutter avoidance radius that in turn operates the clutter avoidance logic. Lines may be denoted as "disturbed"

and that factor is taken into account in subsequent processing. By the end of this process, the discreet spectrum is formed: {fk, Ak}. The final portion of the chain is shown in segment C of FIG. 10. Here, whatever operative library is in effect is summoned and run against the discreet spectrum. This processing is serial and includes an important clutter abatement feature. Note that as in the initial RF sweep, the swept or examined bands are set by operational programming. In this case the library contains recommended sub-bands to utilize. This will reduce computation loads.

The ultimate assessment stage may be performed in an external PC, but is preferably performed internally in the spectrometer. The baseline algorithm is developed specifically to work in adverse conditions, i.e., many clutter lines and large dynamic range between various lines. The algorithm employs the unique pattern of the library spectrum to detect and verify that pattern within the discreet spectrum. In this process, interference by clutter lines is accounted for and generally defeated, with degradation only when the number of effective usable library lines is too far reduced. Eventually, even this degradation will normally be removed by additional subband examinations. The procedure is piecewise integrable so that there is absolutely no penalty in employing any number of small frequency segments in the computation. One key feature in positive species identification is the observance of a plurality of lines. If a line is missing, it generally implies that the species is not present. However, due to the strong interference in the spectrum by powerful neighboring lines, lines may either be previously marked as "present but distorted" or they may be altogether absent. Both cases are accounted for in the algorithm and the resulting spectrum is then fully diagnosed for the particular species, which if found also is assigned a concentration.

The chemical species library used with the spectrometer is a pure database. It must be populated by spectral measurements nominally performed on the spectrometer, with care in preserving the calibrations. All the absorption lines are not necessarily stored in the library. In particular, weaker lines that are near to or in the noise (clutter) are excluded from the library because they would then confuse the recognition process that otherwise is amply accomplished by assessing only the species' predominant lines. The library super-structure is adaptable depending on the applications. That is, the chemical order of importance is built into the hierarchy so that the most critical species for the application are examined first or more often. The library (preamble) and even the line content can be adjusted to meet these needs prior to use or in mid use, given suitable communications to the unit, or direct operator action if the unit is not in remote use. The subbands may also be used in the signal processing chain quite dynamically. Consider an assessment of a single subband that is quantifiably "poor." The system can then re-act by adding the next subband and refining its output.

Figure 11:
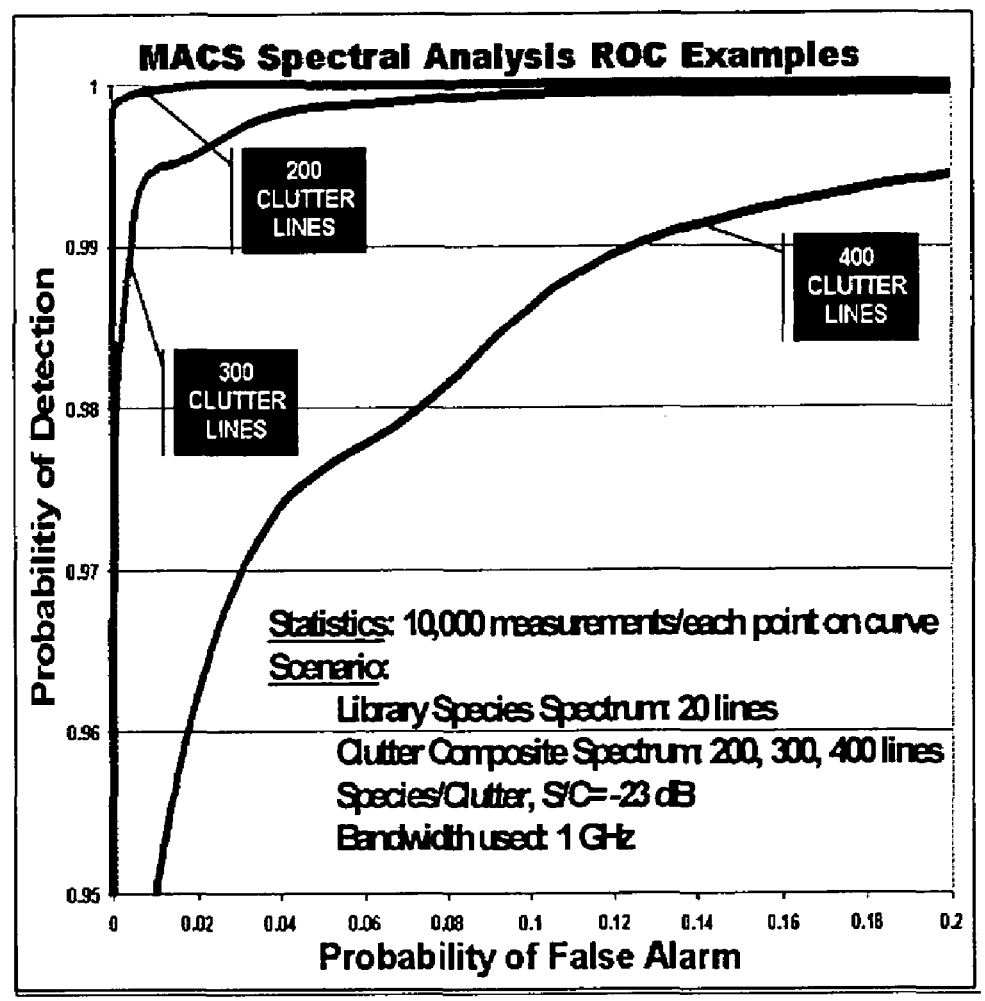
FIG. 11 shows the probability of detection as a function of probability of false alarm.

FIG. 11 shows the effect of clutter on performance of the spectrometer. Some applications of the spectrometer require performance in filed environments outside laboratory setting, in which false alarm avoidance is required. The use of the THz rotational domain is the largest single solution to this problem. That is, intrinsically, the clutter impediment is minimal for submillimeter spectroscopy to other device methodologies. However, clutter degrades the operation if a too limited line set of spectral data of chemical species stored in the library is used and/or if the net frequency interval used is inadequate. To a large extent, both can be controlled, and therefore do not represent a particular threat to the signal processing. The design concept includes a "tunability" feature that allows the system to be adjusted from higher detection probability to higher false alarm avoidance, as needed for the particular device application. It is noteworthy that the issue of false alarms should be put into the context of the application. The submillimeter spectrometer is intrinsically a very general purpose instrument. Given a very large library, a long term monitoring mission of a remote unit may simply issue a periodic report that is essentially a listing of atmospheric content. However, the spectrometer system may be set up to operate a "bell ringer" detector of some species or set of species. Only the first occurrence is relevant and false alarms must not be presented. So in this instance the system should be "tuned" away from the nominal knee of the ROC (nearest the upper left corner of the chart where the ideal system exists with PD=1 and PFA=0) downward toward the lower left region. All of this can be accomplished a priori or during the mission itself, affording the spectrometer systems the highest flexibility.

As described herein, the integrated spectral data can be combined with the GPS position/time and packaged for data communications. The values chosen are, for example, the averaged GPS coordinates and time during the corresponding measurement. Some application may require encryption for security purposes. The use of forward error correction (FEC) or other error correction codes (ECCs) may be used. It may be that a missed data point or two is non-damaging to the application and may not warrant the overhead and complexity of requiring error free communications. Some applications clearly can be best served by a collect and store methodology using a GB-sized disk module that is recovered after a sires of remote sensing. Encryption may still be performed in such applications. In the store and forward methodology, the packaged, integrated and registered (i.e., stamped with position, time and possibly other header information) data can be buffered for eventual transmittal to the A/C communications system for transmission to the remote processing site. In addition, physical parameters employed by the system (namely temperature and pressure readings, or volumetric values if variable volume techniques are required) that are required to calibrate the concentration of the gas sample must be returned with the sample data. The sample header format would extend to include such values for easy extraction and full time correlation with the sample.

Other embodiments and uses of the invention will be apparent to those skilled in the art from consideration of the specification and practice of the invention disclosed herein. All references and written material cited herein for any reason are specifically and entirely incorporated by reference. It is intended that the specification and examples be considered exemplary only with the true scope and spirit of the invention indicated by the following claims.

The invention claimed is:
1. A spectroscopic method comprising:
energizing a solid-state oscillator to generate a submillimeter wave and to sweep a predetermined frequency band;
introducing the submillimeter wave during the sweep into a sample cell that contains a fluid;
electrically generating frequency markers sequentially during the sweep;
reading during the sweep outputs of a solid-state detector disposed in the sample cell; and detecting an absorption of the fluid;
recording the read outputs of the solid-state detector as a function of time and recording the frequency markers as a function of time; and converting the recorded outputs of the solid-state detector into a function of frequency using the recorded frequency markers.

2. The spectroscopic method of claim 1, wherein the frequency markers are generated based on an output of the solid-state oscillator.

3. The spectroscopic method of claim 1, wherein the frequency markers are generated by mixing an output of the solid-state oscillator with an output of a crystal reference oscillator.

4. The spectroscopic method of claim 1, wherein the frequency markers are generated by mixing and amplifying an output of the solid-state oscillator.

5. The spectroscopic method of claim 1, wherein the solid-state oscillator is a VCO of resonant frequency between 5 and 20 GHz.

6. The spectroscopic method of claim 1, further comprising amplifying or multiplying an output of the sold-state oscillator to generate the submillimeter wave.

7. The spectroscopic method of claim 1, wherein the width of the frequency band swept by the solid-state oscillator is approximately 30 GHz.

8. The spectroscopic method of claim 1, wherein the center of the frequency band swept by the solid-state oscillator is between 300 GHz and 400 GHz.

9. The spectroscopic method of claim 1, wherein the center of the frequency band swept by the solid-state oscillator is between 200 GHz and 500 GHz.

10. The spectroscopic method of claim 1, further comprising tuning the sweep of the frequency band into a frequency subband.

11. The spectroscopic method of claim 10, wherein the frequency subband has a width between 10 GHz and 100 KHz.

12. The spectroscopic method of claim 10, further comprising positioning the frequency subband within the frequency band to avoid a background absorption.

13. The spectroscopic method of claim 1, further comprising selecting the outputs of the solid-state detector that are correlated to the frequency markers in a time sequence of recoding, and utilizing only the selected outputs for the converting of the recorded outputs.

14. The spectroscopic method of claim 1, further comprising selecting the outputs of the solid-state detector by an amplitude thereof, and using only the selected outputs for the converting of the recorded outputs.

15. The spectroscopic method of claim 1, wherein the reading of the outputs comprises integrating the outputs for a time period of 1 microsecond to 1 second.

16. A method of measuring submillimeter absorption, comprising:
    introducing a fluid containing a chemical species of interest into a trap;
    cooling the trap so that the chemical species is in a condensed state;
    reducing pressure of the trap to evacuate a remainder of the fluid that is not condensed;
    heating the trap to a first temperature so that the chemical species evaporates;
    drawing the evaporated chemical species into a sample cell; measuring absorption of the chemical species;
    recording read outputs of a solid-state detector as a function of time and recording frequency markers as a function of time; and
    converting the recorded outputs of the solid-state detector into a function of frequency using the recorded frequency markers.

17. The method of measuring submillimeter absorption of claim 16, further comprising keeping the pressure of the sample cell at approximately 10 mTorr during the measuring of the chemical species.

18. The method of measuring submillimeter absorption of claim 16, further comprises heating the trap to a second temperature that is higher than the first temperature after measuring absorption of the chemical species, and repeating the steps of heating to the sample cell and measuring the absorption.

19. The method of measuring submillimeter absorption of claim 18, wherein the fluid contains another chemical species of interest, and the first and second temperatures are determined by the boiling points of the chemical species.

20. A method of surveying an area for a chemical species, comprising:
    taking air into a spectrometer at a first location;
    receiving GPS coordinates at the first location;
    measuring a submillimeter absorption spectrum of the air taken in at the first location;
    recording the absorption spectrum of the first location with the GPS coordinates of the first location as a function of time;
    recording frequency markers of the first location as a function of time;
    converting the recorded outputs of the first location into a function of frequency using the recorded frequency markers;
    taking air into a spectrometer at a second location;
    receiving GPS coordinates at the second location;
    measuring a submillimeter absorption spectrum of the air taken in at the second location;
    recording the absorption spectrum of the second location with the GPS coordinates of the second location as a function of time;
    recording frequency markers of the second location as a function of time; and
    converting the recorded outputs of the second location into a function of frequency using the recorded frequency markers.

21. The method of surveying of claim 20, further comprising sending the recorded spectra and the corresponding GPS coordinates to a receiving station over a wireless network.

22. A spectrometer for measuring submillimeter absorption, comprising:
    a solid-state exciter generating a submillimeter wave and sweeping a predetermined frequency band;
    a frequency marker generating unit electrically generating frequency markers;
    a sample cell to contain a fluid;
    a solid-state detector detecting a submillimeter absorption of the fluid; and
    a control system for reading during the sweep outputs of the solid-state detector, recording the read outputs of the solid-state detector as a function of time, recording the frequency markers as a function of time, and converting the recorded outputs of the solid-state detector into a function of frequency using the recorded frequency markers.

23. The spectrometer of claim 22, wherein the solid-state exciter comprises a solid-state oscillator.

24. The spectrometer of claim 23, wherein the frequency marker generating unit comprises a crystal reference oscillator that is configured to mix with the solid-state oscillator.

25. The spectrometer of claim 23, wherein the solid-state oscillator comprises a VCO of resonant frequency between 5 and 20 GHz.

26. The spectrometer of claim 22, wherein the solid-state exciter further comprises an amplifier and a multiplier.

27. The spectrometer of claim 22, wherein the frequency marker generating unit comprises a low pass filter and an amplifier.

28. The spectrometer of claim 22, further comprising a sample trap connected to an upstream side of the sample cell.

29. The spectrometer of claim 28, wherein the sample trap comprises a micro thermoelectric cooler.

* * * * *